United States Patent [19]

Gomringer

[11] Patent Number: 5,062,648
[45] Date of Patent: Nov. 5, 1991

[54] SEAL FOR ROTATING TORQUE TUBE WITH SEAL VALVE

[75] Inventor: Gary G. Gomringer, Escondido, Calif.

[73] Assignee: InterVentional Technologies, Inc., San Diego, Calif.

[21] Appl. No.: 496,883

[22] Filed: Mar. 21, 1990

Related U.S. Application Data

[63] Continuation-in-part of Ser. No. 413,003, Sep. 26, 1989.

[51] Int. Cl.$^5$ ............... F16J 15/18; A61M 25/00; F16K 15/14
[52] U.S. Cl. .................... 277/112; 137/846; 277/64; 277/115; 277/181; 606/159
[58] Field of Search ............... 277/112, 110, 102, 187, 277/189, 32, 58, 64, 115, 181; 606/159; 137/844, 846; 251/214

[56] References Cited

U.S. PATENT DOCUMENTS

| | | |
|---|---|---|
| 52,742 | 2/1866 | Prindle ................... 277/189 X |
| 657,007 | 8/1900 | Richter ................... 137/846 X |
| 831,139 | 9/1906 | Bonner ................... 277/110 X |
| 1,603,556 | 10/1926 | Platt et al. ................... 277/110 |
| 2,204,915 | 6/1940 | Sharp ................... 277/117 |
| 2,270,054 | 1/1942 | Hogan ................... 277/189 |
| 2,328,382 | 8/1943 | Langdon ................... 137/846 X |
| 2,605,784 | 8/1952 | Snider ................... 137/846 |
| 2,688,329 | 9/1954 | Wallace . |
| 2,721,749 | 10/1955 | Crow ................... 277/110 |
| 2,745,687 | 5/1956 | Stack ................... 277/110 |
| 2,831,714 | 4/1958 | Thorburn ................... 277/112 |
| 3,048,362 | 8/1962 | Scarborough ................... 251/214 |
| 3,091,471 | 5/1963 | Lawless et al. ................... 277/112 |
| 3,155,110 | 11/1964 | Hoffman ................... 137/846 X |
| 3,284,145 | 11/1966 | Bixby ................... 384/484 |
| 3,467,101 | 9/1969 | Fogarty et al. . |
| 3,469,825 | 9/1969 | DuBois ................... 251/214 X |
| 3,547,103 | 12/1970 | Cook . |
| 3,605,725 | 9/1971 | Bentov . |
| 3,731,671 | 5/1973 | Mageoh . |
| 3,901,272 | 8/1975 | Banners et al. ................... 137/846 X |
| 3,913,568 | 10/1975 | Carpenter . |
| 4,195,637 | 4/1980 | Gruntzig et al. . |
| 4,307,722 | 12/1981 | Evans . |
| 4,320,762 | 3/1982 | Bentov . |
| 4,375,011 | 2/1983 | Grümau ................... 277/112 X |
| 4,444,188 | 4/1984 | Bazell et al. . |
| 4,456,017 | 6/1984 | Miles . |
| 4,545,390 | 10/1985 | Leary . |
| 4,571,240 | 2/1986 | Samson et al. . |
| 4,582,181 | 4/1986 | Samson . |
| 4,589,412 | 5/1986 | Kensey . |
| 4,627,436 | 12/1986 | Leckrone . |
| 4,650,467 | 3/1987 | Bonello et al. . |
| 4,669,469 | 6/1987 | Gifford, III et al. ................... 606/159 |
| 4,679,557 | 7/1987 | Opie et al. . |
| 4,728,319 | 3/1988 | Masch . |
| 4,732,154 | 3/1988 | Shiber . |
| 4,895,166 | 1/1990 | Farr et al. ................... 606/159 X |

FOREIGN PATENT DOCUMENTS 107100 6/1917 United Kingdom ................... 277/112

Primary Examiner—Allan N. Shoap
Attorney, Agent, or Firm—Nydegger & Associates

[57] ABSTRACT

A device for establishing a fluid-tight seal around a rotatable drive shaft has a housing which is formed with a straight bore through which the drive shaft is positioned. The bore has a narrow portion, a wide portion and a tapered portion between the narrow and wide portions. A beveled annular seal is positioned in the wide portion of the bore around the drive shaft with the bevel abutting the side of the tapered portion of the bore. An actuator is engaged to the housing and is movable to urge the seal against the tapered portion of the bore to constrict the seal around the drive shaft and establish a fluid-tight seal between the drive shaft and the annular seal. The housing further includes an expanded conforming portion. A flexible seal valve is positioned in the expanded portion to receive the drive shaft. A seal valve has a deformable wedge-shaped portion terminating in a normally closed slit when the shaft is removed. The seal valve prevents leakage when the shaft is inserted into or withdrawn from the housing.

26 Claims, 3 Drawing Sheets

SEAL FOR ROTATING TORQUE TUBE WITH SEAL VALVE

This application is a continuation-in-part of prior copending application entitled "Seal for Rotating Torque Tube", Ser. No. 413,003 filed Sept. 26, 1989.

FIELD OF THE INVENTION

The present invention pertains to devices and apparatus which can be used to establish fluid-tight seals between separate structural elements. More particularly, the present invention pertains to devices and apparatus which are useable to establish fluid-tight seals between structural elements that move relative to each other, and to maintain the fluid-tight seals when the structural elements are adjusted or disconnected. The present invention is particularly, but not exclusively, useful for establishing a fluid-tight seal around a rotatable drive shaft, and for maintaining such a fluid-tight seal during insertion or removal of the shaft from an associated rotating drive assembly.

BACKGROUND OF THE INVENTION

Numerous examples can be cited wherein some sort of fluid-tight seal is either desirable or necessary. In the medical field, for instance, fluid-tight seals are required for medical devices whenever there is a need to either prevent the loss of fluid or prevent fluid from becoming tainted by contact or interaction with a contaminant. Regardless of the particular application, however, the problems which must be overcome to establish a fluid-tight seal are particularly troublesome when the seal is required between elements that move relative to each other.

Not surprisingly, advances in any particular technology frequently involve new developments in related technologies. For example, many related but different developments have been made in the atherectomy field. Very briefly, atherectomy devices are used in vascular surgery to open stenotic segments in arteries by removing plaque from the arterial wall. In performing such surgery, atherectomy devices have some unique requirements which result from their mechanical requirements. Specifically, atherectomy devices have rotating parts which must be able to function simultaneously both inside and outside the body without causing an excessive loss of blood. For example, the atherectomy device disclosed in co-pending application Ser. No. 213,691 for an invention entitled "Cutter for Atherectomy Device" and which is assigned to the same assignee as the present invention, requires the rotation of a cutter element inside an artery by an external drive unit to excise the plaque from the artery. Since both the rotating cutter and the rotating drive shaft must be positioned within the artery and operated by apparatus external to the body, there is a need to provide some means whereby their simultaneous operation can be controlled without an excessive loss of blood. Further, it happens that various sized drive shafts, having different diameters, may need to be used. Additionally, it may be necessary to change drive shafts or cutters and it may also be necessary to rotate the drive shafts at high rotational speeds for extended periods of time. To help this, the drive shaft and cutter are typically placed inside a catheter sheath which establishes access to the artery and which can extend into the artery to effectively isolate the rotating elements of the atherectomy device from direct contact with any tissue other than the plaque which is to be removed. Despite such precautions, however, blood enters the sheath and, consequently, fluid-tight seals are necesary to prevent the loss of blood through the gaps between the sheath and the rotating drive shaft. Fluid-tight seals must also be maintained while changing drive shafts. As will be appreciated, this can involve moving various drive shafts into and out of the sheath. Accordingly, the specific interest of the present invention is maintaining fluid-tight seals which are necessary for the proper operation of an atherectomy device.

In light of the above, it is an object of the present invention to provide a device for establishing a fluid-tight seal around a rotatable drive shaft which is operable with drive shafts of different diameters. Another object of the present invention is to provide a device for establishing a fluid-tight seal around a rotatable drive shaft which allows drive shafts to be changed or substituted for one another. A further object of the present invention is to provide a device which allows various drive shafts to be changed or substituted one for another without loss of fluid. Still another object of the present invention is to provide a device for establishing a fluid-tight seal around a rotatable drive shaft which can withstand substantial fluid pressures. Yet another object of the present invention is to provide a device for establishing a fluid-tight seal around a rotatable drive shaft which is easy to operate, is relatively easy to manufacture and is comparatively cost-effective.

SUMMARY OF THE INVENTION

A device for establishing a fluid-tight seal around a rotatable drive shaft comprises an annular seal member, a housing for holding the seal member around the shaft, and an actuator which urges the seal member against the housing to establish the fluid-tight seal by constricting the seal member against the shaft. The device also includes a seal valve mounted in the housing which automatically closes to prevent loss of fluid when the shaft is removed from the housing. Specifically, the housing is a rigid member that is formed with a longitudinal bore through which the drive shaft is positioned. Further, this bore is formed with a narrow tubular portion, a wide tubular portion which is axially aligned with the narrow portion, and a tapered portion which provides a transition between the wide and the narrow portions.

The seal member of the present invention is an annular tube which is beveled to form an aperture at one end, and which has a radial ring extending peripherally from its outer surface. Additionally, the seal member has a radial groove formed into its inner surface. In its cooperation with the housing, the seal member is seated in the wide portion of the bore with its beveled end abutting the tapered portion of the bore to align the aperture of the seal member with the narrow portion of the bore. As so seated, the ring on the outer surface of the seal member is in a fluid-tight engagement with the surface of the wide portion.

The actuator is a tubular-shaped member which is formed with a longitudinal passageway that is axially aligned with the bore of the housing when the actuator and housing are engaged. As an interconnecting element, the actuator has threads which are threadably engageable with the housing. Also, it has a detent ring which is snappingly engageable with the groove of the seal member to hold the seal member against the actuator. Thus, any relative movement between the actuator and the housing which results from rotation of the actuator, also causes relative movement between the seal member and the housing. Specifically, as the actuator is rotated for its advancement into the bore of the housing, the actuator urges the beveled end of the seal member against the tapered portion of the housing. This interaction between the seal member and the housing causes the aperture of the seal member to constrict. Consequently, with a drive shaft positioned through the passageway of the actuator and on through the bore of the housing, constriction of the aperture causes the seal member to establish a fluid-tight seal between the drive shaft and the seal member. Conversely, when the actuator is rotated for its withdrawal from the bore of the housing, the seal member is pulled from the tapered portion of the bore. As a consequence, this movement opens the aperture and disengages the seal member from the drive shaft to break the fluid-tight seal that was established therebetween.

In another embodiment, the narrow portion of the housing has an expanded conforming portion that includes an annular groove into which a seal valve is seated. Specifically, the seal valve has a hollow cylindrical base which includes an outer annular ring portion that is shaped to fit into the annular groove of the expanded conforming portion. Integral with the base of the seal valve is a hollow wedge-shaped portion formed by a pair of flexible flaps. The flexible flaps taper from the cylindrical base to form a long narrow aperture or slit, and are resiliently biased together so the slit is normally closed. The flaps are sufficiently flexible to allow a drive shaft to be placed through the slit of the seal valve, yet the flaps are sufficiently firm so that when the shaft is removed from the seal valve, the flaps are biased together to close the slit and form a fluid barrier across the housing. Additionally, flaps of the seal valve can close around the shaft to help prevent flow of fluid through the housing while the shaft is operationally inserted through the housing. The seal valve is positioned so that the annular ring portion of the seal valve fits into the annular groove of the housing, with the wedge-shaped portion located in the expanded narrow portion of the housing.

Stated differently, in its cooperation with the housing, the seal valve is seated so that the annular ring engages the radial groove in the interior surface of the housing to establish a fluid-tight engagement between the seal valve and the housing. As situated, the seal valve is positioned with the hollow wedge-shaped portion positioned pointing in a direction the same as the direction of insertion of the drive shaft. Thus, when the drive shaft is positioned through the passageway of the actuator and on through the bore of the housing, it enters the open end of the cylindrical base of the seal valve and exits through the slit at the opposite end of the wedge-shaped portion. Each flap which forms the wedge-shaped portion deforms to accommodate the drive shaft. Each flap, however, is sufficiently flexible and resilient to seal onto the shaft and help prevent leakage around the shaft and to return to its original wedge shape for closing the slit after the drive shaft is withdrawn from the seal valve.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
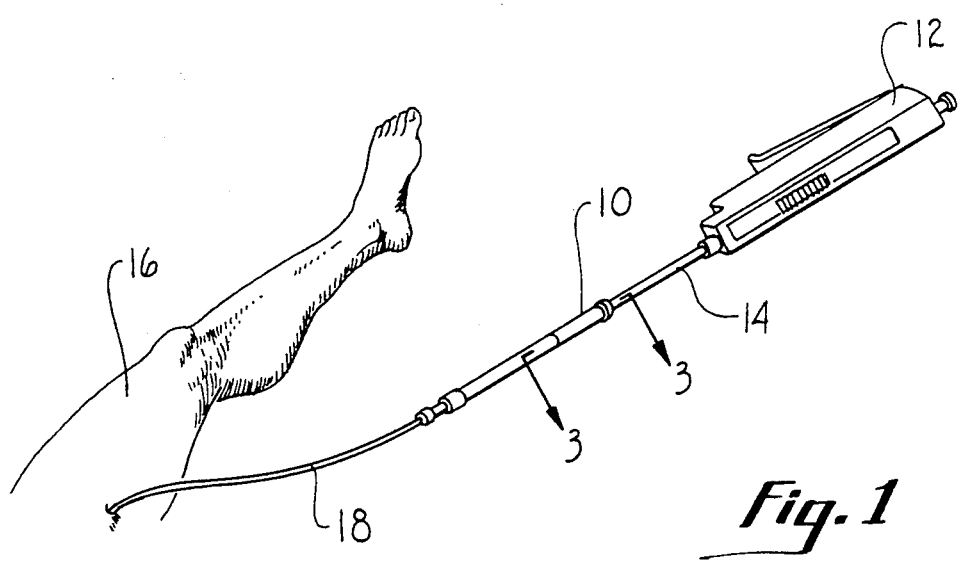
FIG. 1 is a perspective view of the device of the present invention shown in combination with an atherectomy apparatus.

Referring initially to FIG. 1, the device for establishing a fluid-tight seal around a rotatable drive shaft is shown and designated 10. As shown, the device 10 is used in an atherectomy system essentially comprising a drive unit 12 which rotates both a drive shaft 14 and a cutter (not shown) that is attached to the drive shaft 14. A sheath 18 is engaged in a fluid-tight attachment with the device 10 and extends from the device 10 into an artery of patient 16. Sheath 18 thus surroundingly receives the drive shaft 14 and cutter (not shown). In its surrounding position, the sheath 18 isolates the rotating drive shaft 14 from direct contact with body tissue other than that which is to be excised from the stenotic segment of the artery by the rotating action of the cutter. A complete description of an atherectomy system in which the device 10 of the present invention may be used is provided in co-pending patent application Ser. No. 213,691 for an invention entitled "Cutter for Atherectomy Device" which is assigned to the same assignee as the present invention.

Figure 2:
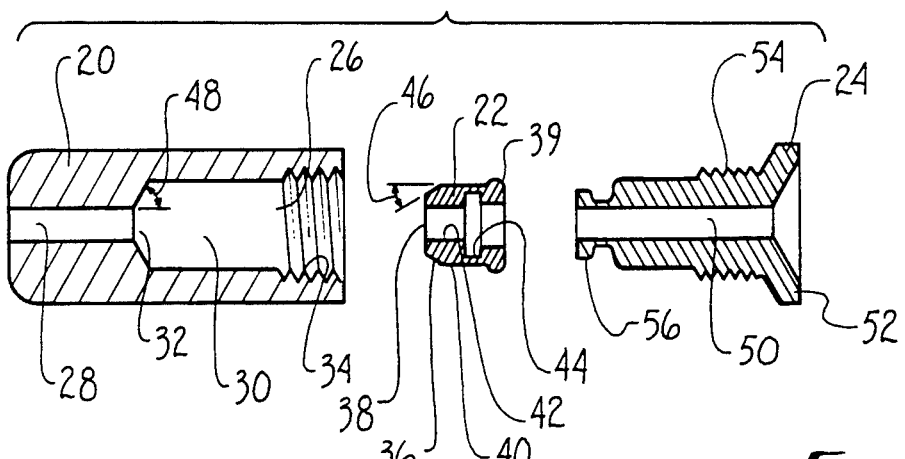
FIG. 2 is an exploded view of the device of the present invention with its components shown in cross section for clarity.

In FIG. 2, it will be more easily seen that device 10 comprises a housing 20, a seal member 22, and an actuator 24. Specifically, housing 20 is a cylindrical-shaped component which is formed with a bore 26 that has a narrow portion 28, a wide portion 30 and a tapered portion 32 which is intermediate narrow portion 28 and wide portion 30. As shown in FIG. 2, wide portion 30 is formed with threads 34 which provide means for engaging housing 20 with actuator 24 for purposes to be subsequently disclosed. Preferably, housing 20 is made of a rigid material such as a plastic or a metal.

The seal member 22, as shown in FIG. 2, is tubular-shaped and has a beveled end 36 which surrounds and defines an aperture 38. Distanced from the beveled end 36 on seal member 22, is a raised ring 39 which is formed radially on the outer surface 40 of member 22 and which extends peripherally around the member 22. On the inner surface 42 of seal member 22, a groove 44 is formed for a purpose to be subsequently discussed. Preferably, seal member 22 is made of a resilient elastomeric material such as rubber. For purposes of comparison, it is preferable that the bevel angle 46 defined between the surface 40 of member 22 and the surface of beveled end 36 be smaller than the taper angle 48 which defines the transition from narrow portion 28 to tapered portion 32. This is so, as will become more apparent after subsequent disclosure, in order to ensure the constriction of aperture 38 whenever beveled end 36 of seal member 22 is urged against tapered portion 32 in bore 26 of housing 20.

The actuator 24 of device 10 is shown in FIG. 2 as an elongated member which has a passageway 50 formed longitudinally through the actuator 24. A knob 52 is formed on actuator 24 for rotating the actuator 24 and a threaded shaft 54 is created to provide for a threadable engagement of the actuator 24 with housing 20. Actuator 24 also has a radial engagement flange 56 which is snappingly engageable with groove 44 of seal member 22 to hold seal member 22 onto actuator 24.

Figure 3A:
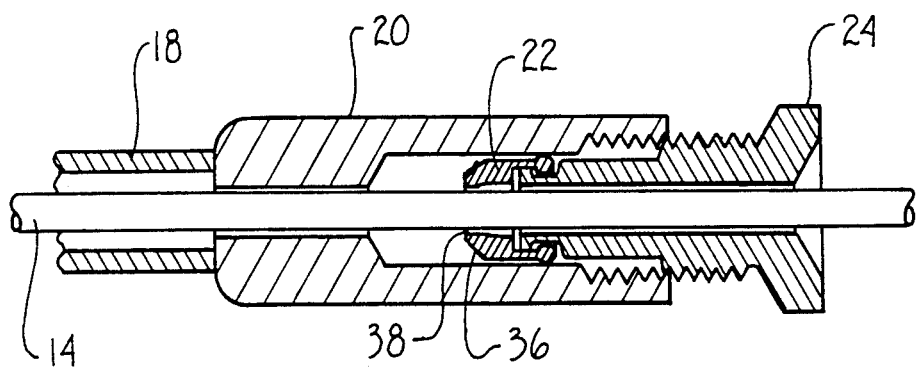
FIG. 3A is a cross-sectional view of the device as seen along the line 3—3 in FIG. 1 with the seal member disengaged from the drive shaft.

The cooperation of structure for components of device 10 is perhaps best seen in FIG. 3A wherein it is shown that flange 56 of actuator 24 is seated in the groove 44 of seal member 22 to hold seal member 22 onto actuator 24. Further, threaded shaft 54 of actuator 24 is engaged with the threads 34 of housing 20 to connect actuator 24 with housing 20. This arrangement places the seal member 22 in wide portion 30 of bore 26 and aligns the aperture 38 of seal member 22 with the narrow portion 28 of bore 26 and the passageway 50 of actuator 24. This alignment, as seen in FIG. 3A, allows actuator 24, seal member 22 and housing 20 to receive drive shaft 14, and permits the drive shaft 14 to extend completely through the device 10.

Figure 3B:
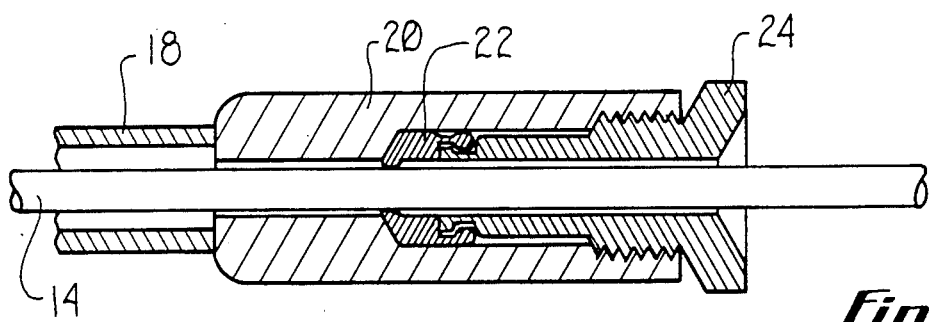
FIG. 3B is a cross-sectional view of the device as seen along the line 3—3 in FIG. 1 with the seal member engaged with the drive shaft.

By comparing FIGS. 3A and 3B, it will be appreciated that actuator 24 is movable together with seal member 22 relative to housing 20. Specifically, in the position shown in FIG. 3A, aperture 38 is released from drive shaft 14 and a fluid-tight seal is not established between the drive shaft 14 and the seal member 22. This configuration permits removal and replacement of drive shaft 14 by the operator as discussed above. On the other hand, when knob 52 is rotated to advance actuator 24 into bore 26 of housing 20, seal member 22 is urged into contact with tapered portion 32 to constrict the aperture 38 onto drive shaft 14 as substantially shown in FIG. 3B. This constriction of aperture 38 onto drive shaft 14 establishes a fluid-tight seal between the drive shaft 14 and seal member 22 while still allowing drive shaft 14 to rotate relative to the seal member 22 and device 10. As will be appreciated by the skilled artisan, the constriction of aperture 38 is enhanced by the difference between bevel angle 46 and taper angle 48 (i.e. bevel angle 46 is less than taper angle 48) which ensures that taper portion 32 collapses beveled end 36 to effectively constrict aperture 38 onto drive shaft 14. Further, it will be appreciated by the skilled artisan that the contact of beveled end 36 against tapered portion 32 will establish a fluid-tight seal between seal member 22 and housing 20. It is also seen in FIGS. 3A and 3B that the ring 39 of seal member 22 engages with the surface of wide portion 30 to create a fluid-tight seal between seal member 22 and housing 20. Thus, as shown in FIG. 3B, with fluid-tight seals between seal member 22 and housing 20, as well as a fluid-tight seal between seal member 22 and drive shaft 14, device 10 provides for a completely fluid-tight engagement of the drive unit 12 with sheath 18. Accordingly, the rotating elements are operable in isolation from other than selected tissue without creating a condition which could inherently cause a loss of body fluids. It will be appreciated by the skilled artisan that proper manipulation of knob 52 on actuator 24 will disengage seal member 22 from the tapered portion 32 of housing 20 to reestablish the configuration shown in FIG. 3A to permit removal or replacement of drive shaft 14.

Importantly, the actuator 24 and seal member 22 are engaged to each other in a desmodromic, or tethered, relationship. Consequently, seal member 22 and actuator 24 are moved in concert. Thus, the advancement of actuator 24 into bore 26 positively engages seal member 22 in a fluid-tight relationship around drive shaft 14. On the other hand, the withdrawal of actuator 24 from bore 26 positively disengages seal member 22 from its engagement with drive shaft 14.

Figure 4A:
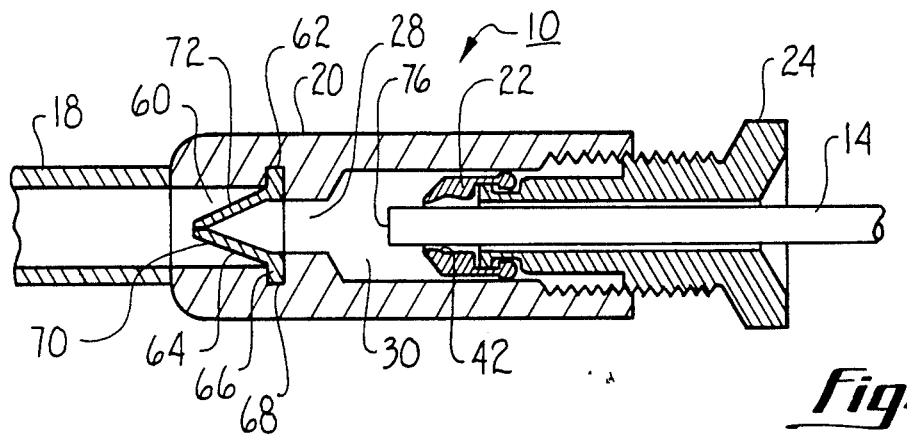
FIG. 4A is a cross-sectional view of an embodiment of the device incorporating a seal valve as seen along the line 3—3 in FIG. 1, with the drive shaft disengaged from the seal valve.
Figure 4B:
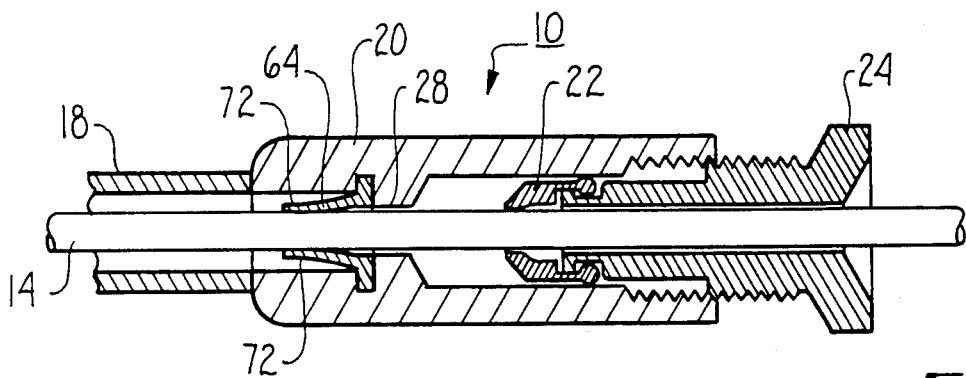
FIG. 4B is a cross-sectional view of the device of FIG. 5A as seen along the line 3—3 in FIG. 1 with the drive shaft engaged with the seal valve, but disengaged from the seal member.
Figure 4C:
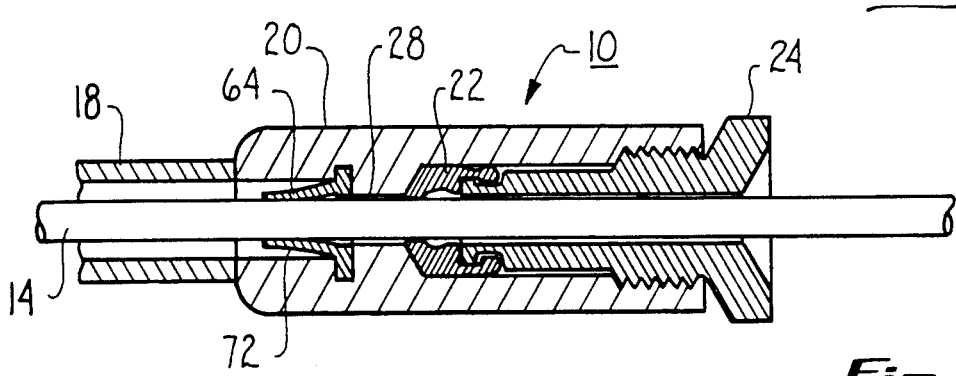
FIG. 4C is a cross-sectional view of the device as seen along the line 3—3 in FIG. 1 with the drive shaft engaged with both the seal valve and with the seal member.
Figure 5A:
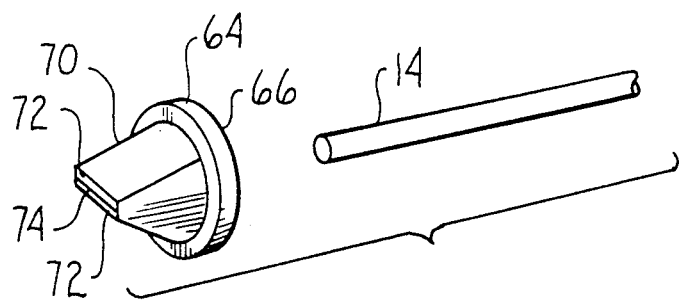
FIG. 5A is a perspective view of the seal valve itself shown disengaged from the drive shaft.
Figure 5B:
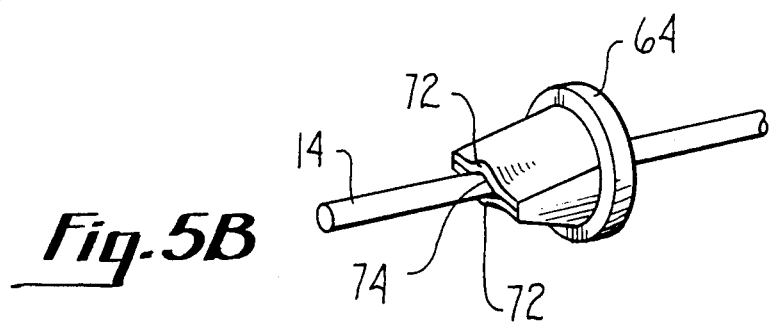
FIG. 5B is a perspective view of the seal valve itself engaged with the drive shaft.

Another embodiment of the present invention is shown in FIGS. 4A, 4B and 4C. In particular, the device 10 includes a housing 20 which has an expanded conforming portion 60, that is adjacent narrow portion 28. Located between conforming portion 60 and narrow portion 28 is an annular groove 62. Seated in annular groove 62 is a seal valve 64, which is preferably made of a resilient elastomeric material such as rubber. Specifically seal valve 64 has a hollow cylindrical base 66, which includes an outer annular ring portion 68 that fits into annular groove 62. Formed onto cylindrical base 66 is a hollow wedge-shaped portion 70. As can perhaps best be appreciated with reference to FIGS. 5A and 5B, wedge-shaped portion 70 of seal valve 64 is formed by a pair of generally flat resiliently flexible flaps 72. Flaps 72 are resiliently biased together and taper from cylindrical base 66 down to a long narrow aperture or slit 74. As shown in FIG. 5A, flaps 72 are biased to be normally closed. Flaps 72 are also flexibly deformable as can be seen in FIG. 5B, to allow a drive shaft 14 to be inserted or placed through slit 74. When shaft 14 is positioned through seal valve 64, flaps 72 envelop shaft 14 to somewhat restrict fluid flow, yet allow movement of shaft 14.

Cooperation of seal valve 64 incorporated in housing 20 can best be seen in FIGS. 4A, 4B and 4C. In FIG. 4A, drive shaft 14 has been inserted through actuator 24, and through seal member 22. As shown in this configuration, end 76 of drive shaft 14 is positioned within wide portion 30 of housing 20. It can be seen that without seal valve 64, if fluid is in wide portion 30, such fluid could possibly leak out of device 10. For example, such leakage might occur around shaft 14 and along inner surface 42 since actuator 24 has not yet been tightened to seat seal member 22 in fluid-tight engagement with shaft 14, as in FIGS. 3B and 4C. Therefore, seal valve 64 is positioned in housing 20, as seen in FIG. 4A to prevent any leaking of fluid from the fluid volume held in sheath 18 into wide portion 30. More importantly, when fluid is held within sheath 18 and the shaft 14 is completely removed from device 10, as would happen when shaft 14 is being replaced, seal valve 64 is needed to prevent fluid flow from sheath 18 out through the device 10. Due to the design of wedge-shaped portion 70, when shaft 14 has been removed, any additional back fluid pressure from the fluid in sheath 18 presses on flap 72 to close seal valve 64, and thereby provide an even tighter fluid-tight seal.

As seen in FIG. 4B, drive shaft 14 can be slidably moved on through slit 74 of hollow seal valve 64 into sheath 18. Again, leakage of fluid is minimized due to the resilient action of flaps 72 which envelop shaft 14, as illustrated in FIG. 5B. Also, fluid pressure on the outside of tapered flaps 72 continues to help maintain a relatively tight seal about shaft 14.

Figure 6:
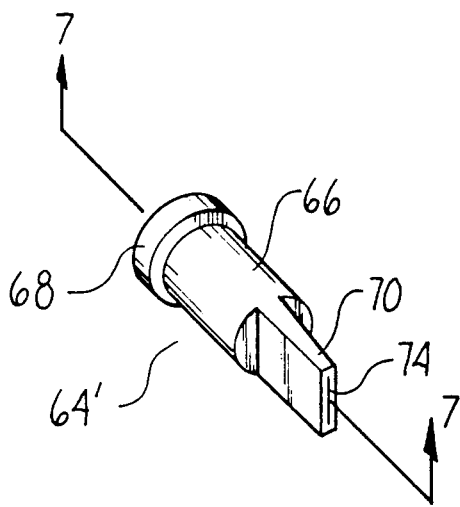
FIG. 6 is a perspective view of an alternative embodiment of the seal valve.
Figure 7:
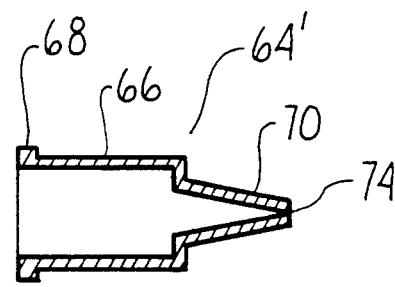
FIG. 7 is a cross-sectional view of the seal valve of FIG. 6 taken along the line 7—7.

There is shown in FIGS. 6 and 7, an alternative embodiment 64' of the seal valve. In this embodiment, hollow cylindrical base 66 is elongated, with outer ring 68 located at an end opposite wedge-shaped portion 70. Hollow cylindrical base 66 has an outer ring 68 which provides a snug fit with groove 62 of expanded narrow portion 60. Thus, seal valve 64' also fits into housing 20 as substantially shown in FIGS. 4A, 4B and 4C, and works similarly to seal valve 64 to provide a closable seal about shaft 14 when it is placed through slit 74.

While the particular seal for rotating torque tube with seal valve as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A device for preventing leakage when establishing a fluid-tight seal around a rotatable drive shaft which comprises:
    resilient means for radially surrounding said drive shaft;
    means for holding said resilient means on said drive shaft;
    means for urging said resilient means against said holding means to constrict said resilient means around said drive shaft to establish a fluid-tight seal; and
    resilient valve means having a reclosable slit and mounted within said holding means for receiving said drive shaft through said slit, said slit being closed when said drive shaft is removed from said valve means to establish said valve means as a fluid barrier.

2. A device for preventing leakage when establishing a fluid-tight seal around a rotatable drive shaft as recited in claim 1, wherein said valve means has a cylindrical base with an outer ring, and said slit is formed by a hollow wedge-shaped portion terminating in a reclosable aperture.

3. A device for preventing leakage when establishing a fluid-tight seal around a rotatable drive shaft as recited in claim 2 wherein said holding means is formed with a longitudinal bore having a relatively narrow portion, a relatively wide portion and a tapered portion intermediate said narrow portion and said wide portion.

4. A device for preventing leakage when establishing a fluid-tight seal around a rotatable drive shaft as recited in claim 3 wherein said resilient means is tube-shaped and has a beveled end defining an aperture and has a raised peripheral ring for abutting said wide portion to establish a fluid-tight seal between said resilient means and said holding means.

5. A device for preventing leakage when establishing a fluid-tight seal around a rotatable drive shaft as recited in claim 4 wherein said urging means is engageable with said holding means and movable with respect thereto to urge said beveled end of said resilient means against said tapered portion of said holding means.

6. A device for preventing leakage when establishing a fluid-tight seal around a rotatable drive shaft as recited in claim 5 wherein said urging means is threadably engaged to said holding means.

7. A device for preventing leakage when establishing a fluid-tight seal around a rotatable drive shaft as recited in claim 5 wherein said resilient means is attached to said urging means and said urging means is movable on said holding means between a first position wherein said aperture is enlarged to release said resilient means from said drive shaft and a second position wherein said aperture of said resilient means is constricted to establish a fluid-tight seal around said drive shaft.

8. A device for preventing leakage when establishing a fluid-tight seal around a rotatable drive shaft as recited in claim 5 wherein said resilient means is made of an elastomeric material.

9. A device for preventing leakage when establishing a fluid-tight seal around a rotatable drive shaft as recited in claim 5 wherein said holding means is made of a rigid material.

10. A device for preventing leakage when establishing a fluid-tight seal around a rotatable drive shaft as recited in claim 5 wherein said urging means is made of a rigid material.

11. A device for preventing leakage when establishing a fluid-tight seal around a rotatable drive shaft which comprises:
    an annular seal having an aperture for receiving said drive shaft therethrough;
    a resilient seal valve having a pair of deformable flexible flaps resiliently biased against one another to form a reclosable aperture for receiving said drive shaft therethrough;
    a housing for holding said annular seal and said seal valve on said drive shaft; and
    an actuator engageable with said housing to squeeze said annular seal therebetween to constrict said aperture and establish a fluid-tight seal around said drive shaft.

12. A device for preventing leakage when establishing a fluid-tight seal around a rotatable drive shaft as recited in claim 11 wherein said housing is formed with a longitudinal bore having a relatively narrow portion, a relatively wide portion and a tapered portion intermediate said narrow portion and said wide portion; and wherein said seal is tube-shaped and has a beveled end around said aperture for abutting said tapered portion of said housing and has a peripheral ring for abutting said wide portion to establish fluid-tight seal between said seal and said housing.

13. A device for preventing leakage when establishing a fluid-tight seal around a rotatable drive shaft as recited in claim 12 wherein said actuator is engageable with said housing and movable with respect thereto to urge said beveled end against said tapered portion.

14. A device for preventing leakage when establishing a fluid-tight seal around a rotatable drive shaft as recited in claim 13 wherein said actuator is threadably engaged to said housing.

15. A device for preventing leakage when establishing a fluid-tight seal around a rotatable drive shaft as recited in claim 13 wherein said seal is attached to said actuator and said actuator is movable on said housing between a first position wherein said aperture is enlarged to release said seal from said drive shaft and a second position wherein said aperture of said seal is constricted to establish a fluid-tight seal around said drive shaft.

16. A device for preventing leakage when establishing a fluid-tight seal around a rotatable drive shaft as recited in claim 13 wherein said seal is made of an elastomeric material.

17. A device for preventing leakage when establishing a fluid-tight seal around a rotatable drive shaft as recited in claim 13 wherein said housing is made of a rigid material.

18. A device for preventing leakage when establishing a fluid-tight seal around a rotatable drive shaft as recited in claim 13 wherein said actuator is made of a rigid material.

19. A device for preventing leakage when establishing a fluid-tight seal around a rotatable drive shaft which comprises:
   a housing formed with a longitudinal bore, said bore having a relatively narrow portion, a relatively wide portion and a tapered portion intermediate said narrow portion and said wide portion, said relatively narrow portion including a conforming portion;
   a resilient seal valve having a flexible aperture for receiving said drive shaft and resiliently closing after said drive shaft is withdrawn from said aperture, said seal valve being seated in said conforming portion of said bore;
   a tube-shaped seal member having a beveled end defining an aperture and having a peripheral ring, said seal member being positioned in said wide portion of said bore with said ring abutting said wide portion to establish a fluid-tight seal between said seal member and said housing and with said beveled end abutting said tapered portion and said aperture in alignment with said bore; and
   an actuator having a passageway, said actuator being engageable with said housing to align said passageway with said aperture and with said bore to receive said drive shaft therethrough and, said actuator being movable on said housing to urge said beveled end of said seal member against said tapered portion of said bore to constrict said aperture and establish a fluid-tight seal around said drive shaft.

20. A device for preventing leakage when establishing a fluid-tight seal around a rotatable drive shaft as recited in claim 19, wherein said seal valve comprises a hollow cylindrical base, and a wedge-shaped portion formed by a pair of deformable flaps which taper from said base to terminate in a reclosable slit, said flaps being resiliently biased together.

21. A device for preventing leakage when establishing a fluid-tight seal around a rotatable drive shaft as recited in claim 20 wherein said actuator is attached to said seal member and said actuator is movable on said housing between a first position wherein said aperture is enlarged to release said seal member from said drive shaft and a second position wherein said aperture is constricted to establish a fluid-tight seal around said drive shaft.

22. A device for preventing leakage when establishing a fluid-tight seal around a rotatable drive shaft as recited in claim 20 wherein said seal is made of an elastomeric material.

23. A device for preventing leakage when establishing a fluid-tight seal around a rotatable drive shaft as recited in claim 20 wherein said housing is made of a rigid material.

24. A device for preventing leakage when establishing a fluid-tight seal around a rotatable drive shaft as recited in claim 20 wherein said actuator is made of a rigid material.

25. A device for preventing leakage when establishing a fluid-tight seal around a rotatable drive shaft which comprises:
   resilient means for radially surrounding said drive shaft;
   means for holding said resilient means on said drive shaft;
   means for selectively urging said resilient means against said holding means to constrict said resilient means around said drive shaft to establish a fluid-tight seal therewith, or distancing said resilient means from said holding means to release said resilient means from said holding means to release said resilient means from said drive shaft to break said fluid-tight seal; and
   valve means having a recloseable slit and mounted within said holding means for receiving said drive shaft through said slit, said slit being closed when said drive shaft is removed from said valve means to establish said valve means as a fluid barrier.

26. A device for preventing leakage when establishing a fluid-tight seal around a rotatable drive shaft as recited in claim 25 wherein said resilient means is attached to said urging means and said urging means is movable on said holding means between a first position wherein said aperture is enlarged to release said resilient means from said drive shaft and a second position wherein said aperture of said resilient means is constricted to establish a fluid-tight seal around said drive shaft.

* * * * *